United States Patent [19]

Floyd et al.

[11] E Patent Number: Re. 33,072

[45] Reissued Date of Patent: Sep. 26, 1989

[54] BENZOTHIAZEPINE DERIVATIVES

[75] Inventors: David Floyd, Pennington; John Krapcho, Somerset, both of N.J.

[73] Assignee: E. R. Squibb & Sons, Inc., Princeton, N.J.

[21] Appl. No.: 219,699

[22] Filed: Jul. 8, 1988

Related U.S. Patent Documents

Reissue of:

[64] Patent No.: 4,584,131
Issued: Apr. 22, 1986
Appl. No.: 746,904
Filed: Jun. 20, 1985

[51] Int. Cl.[4] ..... C07D 281/10; A61K 31/33

[52] U.S. Cl. ..... 540/491

[58] Field of Search ..... 540/491

[56] References Cited

U.S. PATENT DOCUMENTS

| | | | |
|---|---|---|---|
| 3,562,257 | 2/1971 | Kugita et al. | 540/491 |
| 3,646,008 | 2/1972 | Kugita et al. | 540/491 |
| 4,547,495 | 10/1985 | Maiorana et al. | 514/211 |

FOREIGN PATENT DOCUMENTS

| | | | |
|---|---|---|---|
| 900192 | 11/1984 | Belgium | 540/491 |
| 0127882 | 12/1984 | European Pat. Off. | 540/491 |
| 0128462 | 12/1984 | European Pat. Off. | 540/491 |
| 208761 | 4/1987 | New Zealand | 540/491 |

OTHER PUBLICATIONS

Nagao et al., Studies On A New 1,5-Benzothiazepine Derivative (CRD-401). IV, Coronary Vasodilating Effect and Structure-Activity Relationship; Chem. Pharm. Bull. 21(1):92-97 (1973).

*Primary Examiner*—Robert T. Bond
*Attorney, Agent, or Firm*—Lawrence S. Levinson; Donald J. Barrack

[57] ABSTRACT

Vasodilating activity is exhibited by compounds having the formula

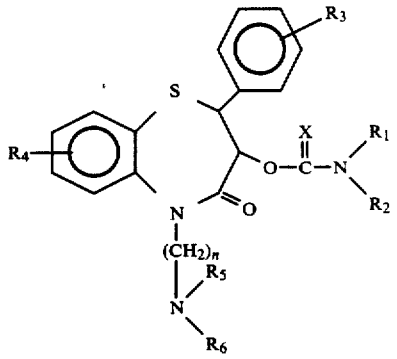

n is 2 or 3;

X is oxygen or sulfur, $R_1$ and $R_2$ are each independently hydrogen alkyl, cycloalkyl, or allyl, or $R_1$ and $R_2$ together with the nitrogen atom to which they are attached are pyrrolidinyl, piperidinyl, or morpholinyl;

$R_3$ is alkyl, alkoxy, halogen, trifluoromethyl, or nitro;

$R_4$ is hydrogen, halogen, trifluoromethyl, or nitro; and $R_5$ and $R_6$ are each independently alkyl or cycloalkyl or $R_5$ and $R_6$ together with the nitrogen atom to which they are attached are pyrrolidinyl, piperidinyl, or morpholinyl.

21 Claims, No Drawings

BENZOTHIAZEPINE DERIVATIVES

Matter enclosed in heavy brackets [ ] appears in the original patent but forms no part of this reissue specification; matter printed in italics indicates the additions made by reissue.

BRIEF DESCRIPTION OF THE INVENTION

Compounds having the formula

I

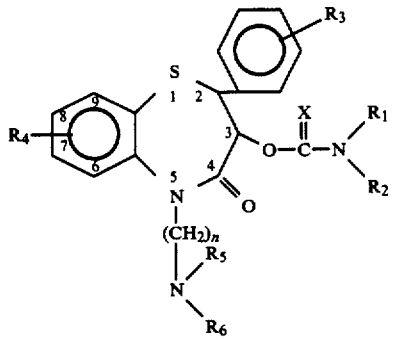

and the pharmaceutically acceptable salts thereof, have useful vasodilating activity. In formula I and throughout the specification, the symbols are as defined below.

n is 2 or 3;

X is oxygen or sulfur;

$R_1$ and $R_2$ are each independently hydrogen alkyl, cycloalkyl, or allyl, or $R_1$ and $R_2$ together with the nitrogen atom to which they are attached are pyrrolidinyl, piperidinyl or morpholinyl;

$R_3$ is alkyl, alkoxy, halogen, trifluoromethyl, or nitro;

$R_4$ is hydrogen, halogen, trifluoromethyl, or nitro; and $R_5$ and $R_6$ are each independently alkyl or cycloalkyl or $R_5$ and $R_6$ together with the nitrogen atom to which they are attached are pyrrolidinyl, piperidinyl, or morpholinyl.

The terms "alkyl" and "alkoxy" refer to both straight and branched chain groups. Those groups having 1 to 10 carbon atoms are preferred.

The term "halogen" refers to fluorine, chlorine, bromine and iodine.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, fumarate, citrate, succinate, benzoate, ascorbate, salicylate, methanesulfonate, benzenesulfonate, toluenesulfonate, lactate and the like.

The carbon atoms in the 3 and 4-positions of the benzothiazepine nucleus of the compounds of formula I are asymmetric carbons. The compounds of formula I, therefore, exist in stereoisomeric forms and as racemic mixtures thereof. This invention is directed to those compounds of formula I which have been described above, wherein the stereochemistry at the chiral centers in the 3 and 4-positions of the benzothiazepine nucleus is d-cis.

DETAILED DESCRIPTION OF THE INVENTION

The compounds of formula I, and the pharmaceutically acceptable salts thereof, are useful as cardiovascular agents. These compounds act as vasodilators and are useful as anti-hypertensive agents. By the administration of a composition containing one(or a combination) of the compounds of this invention the blood pressure of a hypertensive mammalian (e.g., human) host is reduced. Daily doses of about 0.1 to 100 mg. per kilogram of body weight per day, preferably about 1 to about 50 mg. per kilogram per day, are appropriate to reduce blood pressure, and can be administered in single or divided doses. The substance is preferably administered orally, but parenteral routes as the subcutaneous, intramuscular, or intravenous routes can also be employed.

As a result of the vasodilating activity of the compounds of formula I, it is believed that such compounds in addition to being anti-hypertensives may also be useful as antiarrhythmic agents, as anti-anginal agents, as antifibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be prepared by first reacting a compound having the formula

II

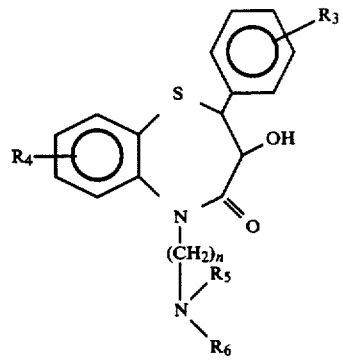

with phosgene or thiophosgene to yield a compound having the formula

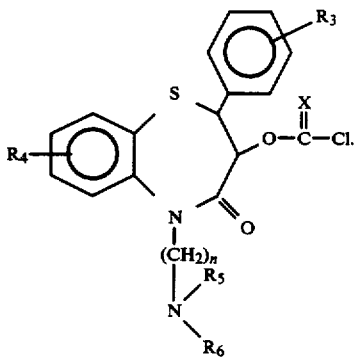

III

An intermediate of formula III (which need not necessarily be isolated) can then be reacted with the appropriate amine (or ammonia) having the formula $$NHR_1R_2 \qquad (IV)$$

to yield the desired product of formula I.

An alternative method for preparing the compounds of formula I wherein one of $R_1$ and $R_2$ is hydrogen comprises reacting a compound of formula II or its sodium salt, with an isocyanate or isothiocyanate having the formula $$R_1N{=}C{=}X \qquad (V)$$

in an inert organic solvent (e.g., acetonitrile, dichloromethane, tetrahydrofuran, benzene or toluene).

An alternative method for preparing the compounds of formula I wherein neither $R_1$ nor $R_2$ is hydrogen comprises reacting a compound of formula II, preferably as a sodium salt, with a compound having the formula

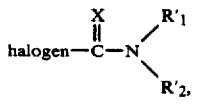

VI wherein $R'_1$ and $R'_2$ are each independently alkyl, cycloalkyl, or allyl, or $R'_1$ and $R'_2$ together with the nitrogen atom to which they are attached are pyrrolidinyl, piperidinyl or morpholinyl.

The starting benzothiazepines of formula II are readily obtainable utilizing prior art methodology; see, for example, U.S. Pat. No. 3,562,257 and Chem. Pharm. Bull., 21:92 (1973).

The following examples are specific embodiments of this invention.

EXAMPLE 1

(d-cis)-5-[2-(Dimethylamino)ethyl]-2,3-dihydro-2-(4-methoxyphenyl)-3-[[(methylamino)carbonyl]oxy]-1,5-benzothiazepin-4(5H)-one, monohydrochloride (d-cis)-5-[2-(Dimethylamino)ethyl]-2,3-dihydro-3-hydroxy-2-(4-methoxyphenyl)-1,5-benzothiazepin-4(5H)-one (4.17 g) was dissolved in 25 ml of acetonitrile, stirred and treated dropwise with 6.4 g (111 mole) of methyl isocyanate. After stirring for 24 hours at room temperature, the solution was concentrated on a rotary evaporator to give 5.13 g of a solid. This material was dissolved in 100 ml of ethyl acetate, extracted twice with 10 ml of water, dried (magnesium sulfate), filtered and the solvent evaporated to give 4.93 g of a foam-like solid. After two recrystallizations from 25 ml isopropanol-100 ml hexane, the material weighed 4.07 g, melting point 76° C., $[\alpha]_D+88.7°$*.

*In these examples, optical rotations were determined on 1% solutions in methanol at room temperature.

Analysis Calc'd for $C_{22}H_{27}N_3O_4S$.isopropanol: C, 61.33; H, 7.21; N, 8.58; S, 6.55; Found: C, 61.31; H, 7.23; N, 8.44; S, 6.58.

The above solvate (4.0 g) was dissolved in 25 ml of warm ethanol, cooled and treated with 1.40 ml of 6.0N hydrogen chloride in ethanol. The resulting solution was diluted with 75 ml of ether to give an oily product which rapidly became granular. After cooling for 3 hours, the solid was filtered and dried (3.81 g), melting point 195°-197° C., $[\alpha]_D+61.3°$. This salt was dissolved in 40 ml of hot acetonitrile and gradually diluted with 40 ml of ether. The product was crystallized from solution, cooled overnight and filtered to give 3.10 g of colorless solid, melting point 194°-196° (dec.), $[\alpha]_D+62.9°$.

Dilution of the above filtrate to 150 ml with ether gave an additional 0.47 g of colorless product, melting point 194°-196° C. (dec.).

Analysis Calc'd for $C_{22}H_{27}N_3O_4S.HCl$: C, 56.70; H, 6.06; N, 9.02; S, 6.88; Cl, 7.60; Found: C, 56,68; H, 6.12; N, 8.98; S, 6.84; Cl, 7.42.

EXAMPLE 2

(d-cis)-5-[2-(Dimethylamino)ethyl]-2,3-dihydro-2-(4-methoxyphenyl)-3-[[(ethylamino)carbonyl]oxy]-1,5-benzothiazepin-4(5H)-one, monohydrochloride To a solution of 4.1 g of (d-cis)-5-[2-dimethylamino)ethyl]-2,3-dihydro-3-hydroxy-2-(4-methoxyphenyl)-1,5-benzothiazepin-4(5H)-one in 25 ml of acetonitrile was added 7.8 g (110 mmol) of ethyl isocyanate portionwise. After standing for 20 hours at room temperature, the solvent was removed on a rotary evaporator to give 5.1 g of a colorless foam-like residue. The material was dissolved in 25 ml of acetonitrile, treated portionwise with 1.8 mol of 6N hydrogen chloride in ethanol and the resulting solution gradually diluted with 100 ml of ether. The hydrochloride salt initially separated as an oil then changed to a granular colorless solid. After cooling overnight, the solid was filtered to give 4.2 g of product, melting point 187°-190° C., $[\alpha]_D+59.2°$. This material was dissolved in 30 ml of warm acetonitrile and gradually diluted with 30 ml of ether. The product separated as large clusters. After cooling overnight, the material was filtered and dried to yield 3.85 g of product, melting point 189°-191° C., $[\alpha]_D+60.0°$.

Analysis Calc'd for $C_{23}H_{29}N_3O_4S.HCl$: C, 57.54; H, 6.09; N, 8.75; S, 6.88; Cl, 7.39; Found: C, 57.57; H, 6.26; N, 8.80; S, 6.69; Cl. 7.56.

EXAMPLE 3

(d-cis)-5-[2-(Dimethylamino)ethyl]-2,3-dihydro-2-(4-methoxyphenyl)-3-[(aminocarbonyl)oxy]-1,5-benzothiazepin-4(5H)-one, monohydrochloride

(A)

(d-cis)-3-[(Chloroformyl)oxy]-5-[2-(dimethylamino)ethyl]-2,3-dihydro-2-(4-methoxyphenyl)-1,5-benzothiazepin-4(5H)-one, monohydrochloride A solution of 4.2 g of (d-cis)-5-[2-(dimethylamino)ethyl]-2,3dihydro-3-hydroxy-2-(4-methoxyphenyl)-1.5-benzothiazepin-4(5H)-one in 25 ml of chloroform was added at 4°-6° C., with stirring to 12 ml of 12.5% phosgene in benzene dissolved in 25 ml of chloroform; a solid separated soon after the addition was begun. After the addition, the mixture was allowed to warm to room temperature to give a yellow solution. After 5 hours, 3 ml more of phosgene solution was added and stirring was continued overnight. After passing in nitrogen to remove excess phosgene, the solvent was removed on a rotary evaporator to give 6.2 g of the title compound as a yellow brittle solid.

(B)

(d-cis)-5-[2-Dimethylamino)ethyl]-2,3-dihydro-2-(4-methoxyphenyl)-3-[(aminocarbonyl)oxy]-1,5-benzothiazepin-4(5H)-one A stirred solution of (d-cis)-3-[(chloroformyl)oxy]-5-[2-(dimethylamino)ethyl]-2,3-dihydro-2-(4-methoxyphenyl)-1,5-benzothiazepin-4(5H)-one, monohydrochloride (6.2 g; 0.011 mol) in 60 ml of dichloromethane was cooled in ice-water and ammonia was passed in for 30 minutes. After the addition of ammonia, the mixture was allowed to warm gradually to room temperature and to stir overnight. The mixture was placed on a rotary evaporator and the bulk of solvent was removed. The yellow foamy residue was stirred with 50 ml of ethyl acetate and 20 ml of water and basified with 2 g of potassium carbonate. The layers were separated and the aqueous phase was extracted three times with ethyl acetate (25 ml). The combined organic layers were washed with saturated sodium chloride (25 ml), dried (magnesium sulfate), and the solvent evaporated to give b 4.4 g of a yellow fluffy amorphous solid. The material was taken up in 20 ml of acetonitrile. On seeding and rubbing, a solid gradually separated. After cooling overnight, the nearly colorless solid was filtered, washed with cold acetonitrile, and air-dried yielding 1.0 g of material. Following recrystallization of 0.97 g of product from 9 ml of hot isopropanol-12 ml of hexane, the colorless product weighed 0.87 g, melting point 179°-181° C., $[\alpha]_D+129°$.

Analysis Calc'd for $C_{21}H_{25}N_3O_4S$: C, 60.70; H, 6.06; N, 10.11; S, 7.72; Found: C, 60.55; H, 6.09; N, 10.00; S, 7.87.

(C)

(d-cis)-5-[2-(Dimethylamino)ethyl]-2,3-dihydro-2-(4-methoxyphenyl)-3-[(aminocarbonyl)oxy]-1,5-benzothiazepin-4(5H)-one, monohydrochloride A suspension of (d-cis)-5-[2-(dimethylamino)ethyl]-2,3-dihydro-2-(4-methoxyphenyl)-3-[(aminocarbonyl-)oxy]-1,5-benzothiazepin-4(5H)-one (0.83 g) in 10 ml of acetonitrile was treated with 0.35 ml of 6N ethanolic hydrogen chloride to give a solution. After evaporating the solvent, the semi-solid residue was taken up in 3 ml of acetonitrile, warmed slightly and diluted with several volumes of ether to precipitate the solid hydrochloride salt. After cooling overnight, the colorless product was filtered under argon, washed with ether, and dried in vacuo; weight, 0.87 g, melting point 161°-164° C. (sinters at 135° C.), $[\alpha]_D+84.4°$.

Analysis Calc'd for $C_{21}H_{25}N_3O_4S.HCl.1.25$ mole of $H_2O$: C, 53.15 H, 6.05; N, 8.86; Cl. 7.47; S, 6.76; Found: C, 53.11; H, 5.75; N, 8.71; Cl, 7.56; S, 6.99.

EXAMPLE 4

(d-cis)-5-[2-(Dimethylamino)ethyl]-2,3-dihydro-2-(4-methoxyphenyl)-3-[[(dimethylamino)carbonyl]-oxy]-1,5benzothiazepin-4(5)-one, monofumarate salt A stirred solution of 3.37 g (9.05 mmol) of (d-cis)-5-[2-(dimethylamino)ethyl]-2,3-dihydro-3-hydroxy-2-(4-methoxyphenyl)-1,5benzothiazepin-4(5H)-one (b 3.37 g, 9.05 mmol) in 120 ml of benzene was treated with 0.7 g (14.6 mmol) of 50% sodium hydride (oil dispersion) and heated to reflux for 1 hour. The yellow-orange solution was cooled to 30° C., freshly distilled dimethylcarbamyl chloride (0.95 ml. 10.3 mmol) was added, and the mixture was stirred at room temperature. After stirring overnight, 120 ml of ether was added, followed by 14 g of potassium carbonate in 35 ml of water. The layers were separated, the organic phase washed with 35 ml of water and 35 ml of saturated sodium chloride solution, dried (magnesium sulfate), and the solvents evaporated to give 4.1 g of a yellow-orange syrup.

The crude base was combined with 1.0 g of base from an earlier experiment by dissolving in 30 ml of methanol, treated with 1.33 g of fumaric acid, warmed slightly to obtain a solution, and diluted to 250 ml with ether. On seeding and rubbing, the solid salt rapidly separated. After cooling overnight, the cream colored solid was filtered, washed with ether, and dried in vacuo yielding 3.87 g of material. Recrystallization of 3.75 g of product from 80 ml of acetonitrile, gave 3.46 g of nearly colorless product, melting point 172°-174° C., sintering at 170° C., $[\alpha]_D+32.3°$.

Analysis Calc'd for $C_{23}H_{29}N_3O_4S.C_4H_4O_4.0.25H_2O$: C, 57.48; H, 5.98; N, 7.45; S, 5.60; Found: C, 57.49; H, 5.96; N, 7.45; S, 5.60.

EXAMPLE 5

(d-cis)-5-[2-Dimethylamino)ethyl]-2,3-dihydro-2-(4-methoxyphenyl)-3-[[(isopropylamino)carbonyl]-oxy]-1,5-benzothiazepin-4(5H)-one Utilizing the procedure of Example 1, but substituting an equivalent quantity of ispropyl isocyanate for the methyl isocyanate, yields the title product.

EXAMPLE 6

(d-cis)-5-[2-(Dimethylamino)ethyl]-2,3-dihydro-2-(4-methoxyphenyl)-3-[[(cyclopropylamino)-carbonyl]oxyl]-1,5-benzothiazepin-4(5H)-one Utilizing the procedure of Example 1, but substituting cyclopropyl isocyanate for the methyl isocyanate, yields the title product.

EXAMPLE 7

(d-cis)-5-[2-(Dimethylamino)ethyl]2,3-dihydro-2-(4-methoxyphenyl)-3-[[(cyclohexylamino)-carbonyl]oxy]-1,5-benzothiazepin-4(5H)-one Utilizing the procedure of Example 1, but substituting cyclohexyl isocyanate for the methyl isocyanate, yields the title product.

EXAMPLE 8

(d-cis)-5-[2-Dimethylamino)ethyl]-2,3-dihydro-2-(4-methoxyphenyl)-3-[[(allylamino)carbonyl]-oxy]-1,5-benzothiazepin-4(5H)-one Utilizing the procedure of Example 1, but substituting allyl isocyanate for the methyl isocyanate, yields the title product.

EXAMPLE 9

(d-cis)-5-[2-Dimethylamino)ethyl]2,3-dihydro-2-(4-methoxyphenyl)-3-[[(piperidino)carbonyl]oxy]-1,5-benzothiazepin-4(5H)-one Utilizing the procedure of Example 3, but substituting two equivalents of piperidine for the ammonia in part B, yields the title product.

EXAMPLE 10

(d-cis)-5-[2-(Dimethylamino)ethyl]-2,3-dihydro-2-(4-methoxyphenyl)-3-[[(morpholino)]carbonyl]oxy]-1,5-benzothiazepin-4(5H)-one Utilizing the procedure of Example 3, but substituting two equivalents of morpholine for the ammonia in part B, yields the title product.

EXAMPLE 11

(d-cis)-5-[2-(Dimethylamino)ethyl]-2,3-dihydro-2-(4-methoxyphenyl)-3-[[(diethylamino)carbonyl]-oxy]-1,5-benzothiazepin-4(5H)-one Utilizing the procedure of Example 4, but substituting diethylcarbamyl chloride for the dimethylcarbamyl chloride, yields the title product.

EXAMPLE 12

(d-cis)-5-[2-(Dimethylamino)ethyl]2,3-dihydro-2-(4-methoxyphenyl)-3-[[(methylamino)thiocarbonyl]-oxy]-1,5-benzothiazepin-4(5H)-one Utilizing the procedure of Example 4, but substituting 5 equivalents of methyl isothiocyanate for the dimethylcarbamyl chloride, yields the title product.

EXAMPLE 13

(d-cis)-5-[2-(Dimethylamino)ethyl]-2,3-dihydro-2-(4-methoxyphenyl)-3-[[(n-propylamino)thiocarbonyl]oxy]-1,5-benzopthiazepin-4(5H)-one Utilizing the procedure of Example 4, but substituting 5 equivalents of n-propyl isothiocyanate for the dimethylcarbamyl chloride, yields the title product.

EXAMPLE 14

(d-cis)-5-[2-(Dimethylamino)ethyl]2,3-dihydro-2-(4-methoxyphenyl)-3-[[(t-butylamino)thiocarbonyl]-oxy]-1,5-benzothiazepin-4(5H)-one Utilizing the procedure of Example 14, but substituting 5 equivalents of t-butyl isothiocyanate for the dimethylcarbamyl chloride, yields the title product.

EXAMPLE 15

(d-cis)-5-[2-(Dimethylamino)ethyl]-2,3-dihydro-2-(4-methoxyphenyl)-3-[(aminothiocarbonyl)oxy]-1,5-benzothiazepin-4(5H)-one Utilizing the procedure of Example 3, but substituting thiophosgene for the phosgene in part A, yields the title product.

EXAMPLE 16

(d-cis)-5-[2-(Dimethylamino)ethyl]-2,3-dihydro-2-(4-methoxyphenyl)-3-[[(dimethylamino)thiocarbonyl]oxy]-1,5-benzothiazepin-4(5H)-one Utilizing the procedure of Example 3, but substituting thiophosgene for the phosgene in part A and then replacing the ammonia with two equivalents of dimethylamine, yields the title product.

EXAMPLE 17

(d-cis)-5-[2-(Dimethylamino)ethyl]-2,3-dihydro-2-(4-methylphenyl)-3-[[(methylamino)carbonyl]-oxy]-1,5-benzothiazepin-4(5H)-one The reaction of (d-cis)-5-[2-(dimethylamino)ethyl]-2,3-dihydro-3-hydroxy-2-(4-methylphenyl)-1,5-benzothiazepin-4(5H)-one with 5 equivalents of methyl isocyanate in acetonitrile according to the method described in Example 1 yields the title product.

EXAMPLE 18

(d-cis)-5-[2-(Dimethylamino)ethyl]2,3-dihydro-2-(4-chlorophenyl)-3-[[(methylamino)carbonyl]oxy]-1,5-benzothiazepin-4(5H)-one The reaction of (d-cis)-5-[2-(dimethylamino)-ethyl]-2,3-dihydro-2-(4-chlorophenyl)-3-hydroxy-1,5-benzothiazepin-4(5H)-one with 5 equivalents of methyl isocyanate in acetonitrile according to the method described in Example 1 yields the title product.

EXAMPLE 19

(d-cis)-5-[2-(Dimethylamino)ethyl]-2,3-dihydro-2-(4-methoxyphenyl)-3-[[(methylamino)carbonyl]oxy]-8-chloro-1,5-benzothiazepin-4(5H)-one The reaction of (d-cis)-5-[2-(dimethylamino)-ethyl]-2,3-dihydro-2-(4-methoxyphenyl)-3-hydroxy-8-chloro-1,5-benzothiazepin-4(5H)-one with 5 equivalents of methyl isocyanate in acetonitrile according to the method described in Example 1 yields the title product.

EXAMPLE 20

(d-cis)-5-[2-(Dimethylamino)ethyl]-2,3-dihydro-2-(4-methoxyphenyl)-3-[[(methylamino)carbonyl]oxy]-8-(trifluoromethyl)-1,5-benzothiazepin-4(5H)-one The reaction of (d-cis)-5-[2-(dimethylamino)-ethyl]-2,3-dihydro-2-(4-methoxyphenyl)-3-hydroxy-8-(trifluoromethyl)-1,5-benzothiazepin-4(5H)-one with 5 equivalents of methyl isocyanate in acetonitrile according to the procedure described in Example 1 yields the title product.

EXAMPLE 21

(d-cis)-5-[2-(Dimethylamino]-2,3-dihydro-2-(4-methoxyphenyl)-3-[[(methylamino)carbonyl]oxy]-7-(trifluoromethyl)-1,5-benzothiazepin-4(5H)-one The reaction of (d-cis)-5-[2-(dimethylamino)-ethyl]-2,3-dihydro-2-(4-methoxyphenyl)-3-hydroxy-7-(trifluoromethyl)-1,5-benzothiazepin-4(5H)-one with 5 equivalents of methyl isocyanate in acetonitrile according to the procedure described in Example 1 yields the title product.

EXAMPLE 22

(d-cis)-5-[3-(Dimethylamino)propyl]-2,3-dihydro-2-(4-methoxyphenyl)-3-[[(methylamino)carbonyl]oxy]-1,5-benzothiazepin-4(5H)-one The reaction of (d-cis)-5-[3-(dimethylamino)-propyl]-2,3-dihydro-2-(4-methoxyphenyl)-3-hydroxy-1,5-benzothiazepin-4(5H)-one with 5 equivalents of methyl isocyanate in acetonitrile according to the procedure described in Example 1 yields the title product.

EXAMPLE 23

(d-cis)-5-[2-(piperidino)ethyl]-2,3dihydro-2-(4-methoxyphenyl)-3-[[(methylamino)carbonyl]oxy]-1,5-benzothiazepin-4(5H)-one The reaction of (d-cis)-5-[2-(piperidino)-ethyl]2,3-dihydro-2-(4-methoxyphenyl)-3-hydroxy-1,5-benzothiazepin-4(5H)-one with 5 equivalents of methyl isocyanate in acetonitrile according to the procedure described in Example 1 yields the title product.

What is claimed is:

1. A compound having the formula

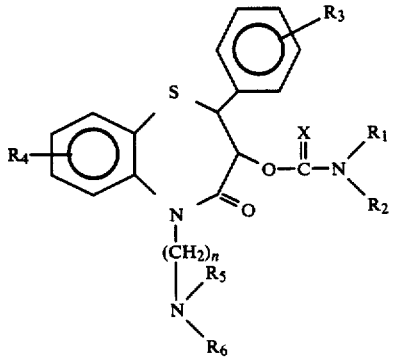

or a pharmaceutically acceptable salt thereof wherein n is 2 or 3;

X is oxygen or sulfur;

$R_1$ and $R_2$ are each independently hydrogen alkyl, cycloalkyl, or allyl [or $R_1$ and $R_2$ together with the nitrogen atom to which they are attached are pyrrolidinyl, piperidinyl or morpholinyl];

$R_3$ is alkyl, alkoxy, halogen, trifluoromethyl, or nitro; and $R_4$ is hydrogen, halogen, or trifluoromethyl, or nitro; and $R_5$ and $R_6$ are each independently alkyl or cycloalkyl or $R_5$ and $R_6$ together with the nitrogen atom to which they are attached are pyrrolidinyl, piperidinyl, or morpholinyl.

2. A compound in accordance with claim 1 wherein X is oxygen.

3. A compound in accordance with claim 1 wherein X is sulfur.

4. A compound in accordance with claim 1 wherein $R_1$ and $R_2$ are each hydrogen.

5. A compound in accordance with claim 1 wherein $R_1$ and $R_2$ are each alkyl.

6. A compound in accordance with claim 1 wherein $R_1$ is hydrogen and $R_2$ is alkyl.

7. A compound in accordance with claim 1 wherein $R_3$ is alkoxy.

8. A compound in accordance with claim 1 wherein $R_3$ is 4-methoxy.

9. A compound in accordance with claim 1 wherein $R_4$ is hydrogen.

10. A compound in accordance with claim 1 wherein $R_4$ is halogen.

11. A compound in accordance with claim 1 wherein $R_4$ is 8-chloro.

12. A compound in accordance with claim 1 wherein $R_5$ and $R_6$ are each alkyl.

13. A compound in accordance with claim 1 wherein $R_5$ and $R_6$ are each methyl.

14. A compound in accordance with claim 1 wherein n is 2.

15. A compound in accordance with claim 1 wherein n is 3.

16. A compound in accordance with claim 1 wherein n is 2, X is oxygen, $R_3$ is 4-methoxy, $R_4$ is hydrogen and $R_5$ and $R_6$ are each methyl.

17. A compound in accordance with claim 1 wherein n is 2, X is oxygen, $R_3$ is 4-methoxy, $R_4$ is 8-chloro and $R_5$ and $R_6$ are each methyl.

18. The compound in accordance with claim 1, (d-cis)-5-[2-(dimethylamino)ethyl]-2,3-dihydro-2(4-methoxyphenyl)-3-[[(methylamino)carbonyl]-oxy]-1,5-benzothiazepin-4(5H)-one, or a pharmaceutically acceptable salt thereof.

19. The compound in accordance with claim 1, (d-cis)-5-[2-(dimethylamino)ethyl]-2,3-dihydro-2-(4-methoxyphenyl)-3-[[(ethylamino)carbonyl]oxy]-1,5-benzothiazepin-4(5H)-one, or a pharmaceutically acceptable salt thereof.

20. The compound in accordance with claim 1, (d-cis)-5-[2-(dimethylamino)ethyl]-2,3-dihydro-2-(4-methoxyphenyl)-3-[(aminocarbonyl)oxy]-1,5-benzothiazepin-4(5H)-one, or a pharmaceutically acceptable salt thereof.

21. The compound in accordance with claim 1, (d-cis)-5-[2-(dimethylamino)ethyl]-2,3-dihydro-2-(4-methoxyphenyl)-3-[[(dimethylamino)carbonyl]-oxy]-1,5-benzothiazepin-4(5H)-one, or a pharmaceutically acceptable salt thereof.

* * * * *